United States Patent [19]

Shiga et al.

[11] Patent Number: 4,927,264
[45] Date of Patent: May 22, 1990

[54] NON-INVASIVE MEASURING METHOD AND APPARATUS OF BLOOD CONSTITUENTS

[75] Inventors: Toshikazu Shiga, Kyoto; Takuji Suzaki, Uji, both of Japan

[73] Assignee: Omron Tateisi Electronics Co., Kyoto, Japan

[21] Appl. No.: 278,494

[22] Filed: Dec. 1, 1988

[30] Foreign Application Priority Data

Dec. 2, 1987 [JP] Japan .................. 62-304975
Dec. 2, 1987 [JP] Japan .................. 62-304976
Dec. 3, 1987 [JP] Japan .................. 62-306481

[51] Int. Cl.$^5$ .................. A61B 5/00; G01N 21/17
[52] U.S. Cl. .................. 356/41; 128/633
[58] Field of Search .................. 356/41; 128/633, 664, 128/665

[56] References Cited

U.S. PATENT DOCUMENTS

| | | | |
|---|---|---|---|
| 4,167,331 | 9/1979 | Nielsen | 356/41 |
| 4,222,389 | 9/1980 | Rubens | 356/41 |
| 4,266,554 | 5/1981 | Hamaguri | 356/41 |
| 4,463,762 | 8/1984 | Rubens | 356/41 |

Primary Examiner—Richard A. Rosenberger
Attorney, Agent, or Firm—Wegner & Bretschneider

[57] ABSTRACT

In order to measure the oxygen saturation in venous blood, a venous blood stream is made time-variant by applying pressure with a peak value of the minimum blood pressure to a proximal portion from a measuring part. Light beams with different wavelengths are transmitted from the measuring part and detected by photodiodes. Photodetected signals are logarithm-converted and venous signal components are separated from logarithm-converted signals with a filter circuit. The oxygen saturation of venous blood is calculated on the basis of separated venous signal components.

8 Claims, 5 Drawing Sheets

NON-INVASIVE MEASURING METHOD AND APPARATUS OF BLOOD CONSTITUENTS

BACKGROUND OF THE INVENTION

The present invention relates to a non-invasive measurement of blood constituents which is adapted to a measurement of oxygen saturation in blood in a living body, etc., and more specifically, relates to a measurement of venous blood constituents in a living body.

Among known non-invasive measuring apparatuses of blood constituents is an apparatus which optically measures those through the application of the Lambert-Beer law. FIG. 1 shows such an apparatus to measure the oxygen saturation, i.e., an existence ratio of oxygenated hemoglobin.

In this figure, light beams emitted from the light source 31 is transmitted through a measuring part, e.g., a finger f, of a living body and are received by photodetectors $33_1$ and $33_2$. The light beams with wavelengths of $\lambda_1$ (e.g., 805 nm) and $\lambda_2$ (e.g., 650 nm) are selected by interference filters $32_1$ and $32_2$, respectively. That is, the light quantities of transmission light beams with wavelength of $\lambda_1$ and $\lambda_2$ are selectively detected.

Output signals from the photodetectors $33_1$ and $33_2$ are processed by respective signal processing circuits $39_1$ and $39_2$ and provided to a multiplexer (MUX) 40. The signal processing circuits $39_1$ comprises a logarithmic amplifier 34, a high-pass filter (HPF) 35, an amplifier 36, a low-pass filter (LPF) 37, and a sample hold (S/H) circuit 38. Another signal processing circuit $39_2$ has the same constition as the signal processing circuit $39_1$.

A received light quantity I of the photodetector is in accordance with the Lambert-Beer law and expressed as:

$$I = I_0 F_T \cdot 10^{-p} \cdot 10^{-q} \tag{1}$$

where $$p = \alpha' \gamma d, \quad q = \alpha \gamma l.$$

In the above equation, $F_T$ denotes an absorption degree by living body tissues; $\alpha$ and $\alpha$, light absorption coefficients of venous blood and arterial blood, respectively; $\gamma$, a blood density; d and l, widths of venous and arterial blood, respectively. The photodetected signal E (voltage value) from the photodetector $33_1$ is expressed as:

$$E = A I_0 F_T \cdot 10^{-p} \cdot 10^{-q} \tag{2}$$

where A denotes a gain of photoelectric conversion including the sensitivity of the photodetector $33_1$.

The logarithmic conversion of the photodetected signal E from the photodetector $33_1$ results in:

$$\log E = \log A I_0 F_T - p - q = \log A I_0 F_T - \alpha' \gamma d - \alpha \gamma l \tag{3}$$

The terms $\log A I_0 F_T$ and $-\alpha' \gamma d$ are signal components of the tissues and venous blood, respectively, and do not vary with time. On the other hand, the term $-\alpha \gamma l$ is a signal component of the arterial blood and therefore varies with time in synchronism with a heartbeat as a ripple signal shown in FIG. 2.

The time-variant signal component of the arterial blood is separated from the other components by the high-pass filter 35. The separated signal component of the arterial blood is amplified by the amplifier 36, filtered by the low-pass filter 37 so as to eliminate hum components originating from a power supply, and held by the sample hold circuit 38. The signal processing circuit $39_2$ performs the same processing as described above, so that the arterial signal component which corresponds to $\lambda_2$ is held by the sample hold circuit therein.

The respective arterial signal components corresponding to $\lambda_1$ and $\lambda_2$ are successively provided to an A/D converter 41 through the multiplexer 40, converted to digital signals, and received by a CPU 42. The CPU 42 calculates the ratio Y of the component $-\alpha_1 \gamma l$ corresponding to $\lambda_1$ to the component $-\alpha_2 \gamma l$ corresponding to $\lambda_2$:

$$Y = \frac{-\alpha_1 \gamma l}{-\alpha_2 \gamma l} = \frac{\alpha_1}{\alpha_2}. \tag{4}$$

The ratio Y can be calculated easily by using an amplitude ratio or waveform area ratio of the arterial signal components.

The CPU 42 further calculates the oxygen saturation $S_a O_2$ on the basis of the following equation (5):

$$S_a O_2 = B - CY \tag{5}$$

where B and C are constants related to absorption coefficients of deoxyhemoglobin and oxyhemoglobin, respectively. The calculated $S_a O_2$ is displayed on a display unit 43.

It is understood that if the oxygen saturation of arterial blood and that of venous blood could be compared, the information concerning the activity of tissues, etc., which is very useful, would be obtained. However, the above-described apparatus cannot measure the oxygen saturation and other blood constituent characteristics (e.g., density) of venous blood.

This is because, for example, there exists hemoglobin in the venous blood as well as in the arterial blood and, as described above, the venous signal component, $-\alpha' \gamma d$, is time-invariant, so that the venous signal component cannot be separated from the signal components of arterial blood and tissues.

SUMMARY OF THE INVENTION

An object of the present invention is to solve the above-described problem, stated more specifically, to provide a method and apparatus for non-invasive measurement of blood constituents, in which venous blood constituents can be detected.

A non-invasive measuring method of a blood constituent according to the invention comprises the steps of: illuminating a measuring part of a living body, detecting emergent light beams from the measuring part by photodetectors, obtaining output signals from the photodetectors corresponding to at least two kinds of light beams with different wavelengths, logarithm-converting the output signals, separating time-variant signal components, and calculating a blood constituent on the basis of the time-variant signal components; and is characterized by the further steps of: applying pressure with a value of about minimum blood pressure to a proximal portion from the measuring part so as to obstruct a venous blood stream, causing variations in venous signal components corresponding to the respective light beams with different wavelengths, separating the venous signal components from the logarithm-converted signals, and calculating the blood constituent in venous blood on the basis of the separated venous signal components.

Other and further objects, features and advantages of the present invention will appear more fully from the following description taken in connection with the accompanying drawings.

DETAILED DESCRIPTION OF THE PREFERRED EMBODIMENTS

Preferred embodiments of the present invention will be hereinafter described with reference to the accompanying drawings.

Figure 1:
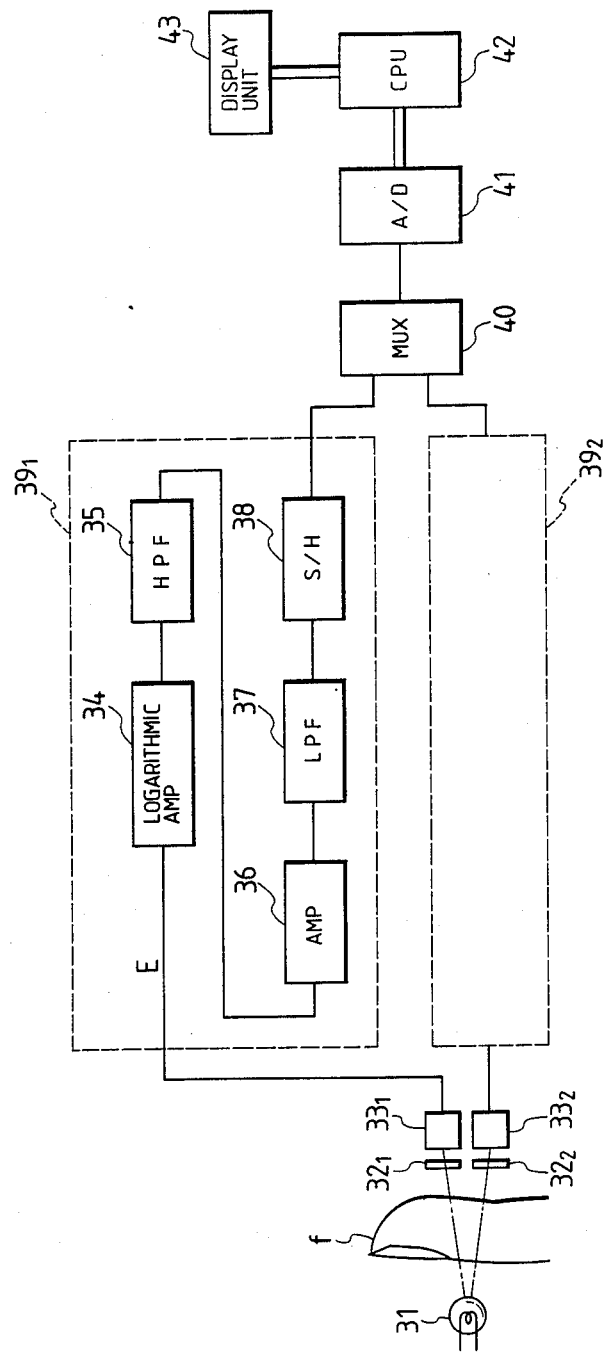
FIG. 1 is a block diagram of a conventional measuring apparatus of the oxygen saturation.
Figure 2:
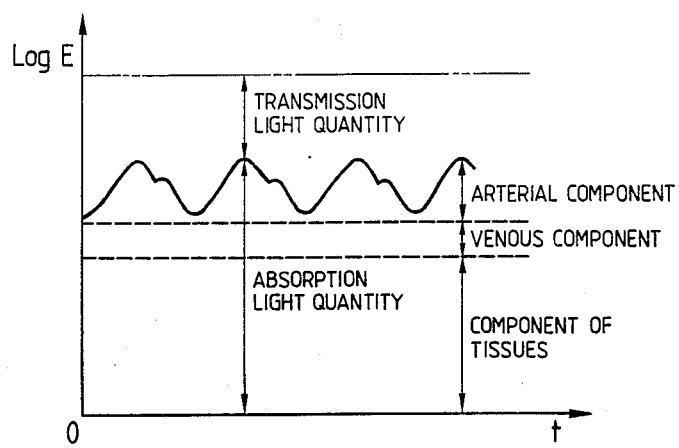
FIG. 2 is a graph showing a waveform of a logarithm-converted photodetected signal.
Figure 3:
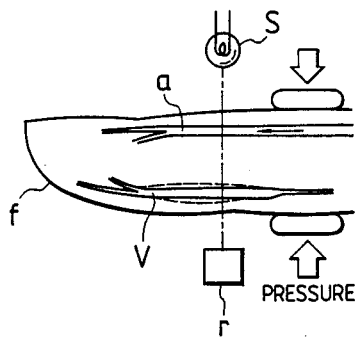
FIG. 3 is a schematic drawing showing an artery and vein in a finger when pressure is applied through a cuff.

In the present invention, a constituent in venous blood is measured by applying pressure to a proximal portion from a measuring part and causing variation in a venous signal component. When the pressure with a value of about minimum blood pressure is applied to that portion, blood streams in veins $\underline{v}$ are obstructed (including the case of complete obstruction). However, as shown in FIG. 3, since blood streams in arteries $\underline{a}$ are not obstructed, blood flows into the veins in the measuring part. As a result, the vein $\underline{v}$ expands as indicated by the dashed lines in FIG. 3 and blood thickness in the vein $\underline{v}$ is increased, so that a larger quantity of light is absorbed there.

Figure 4:
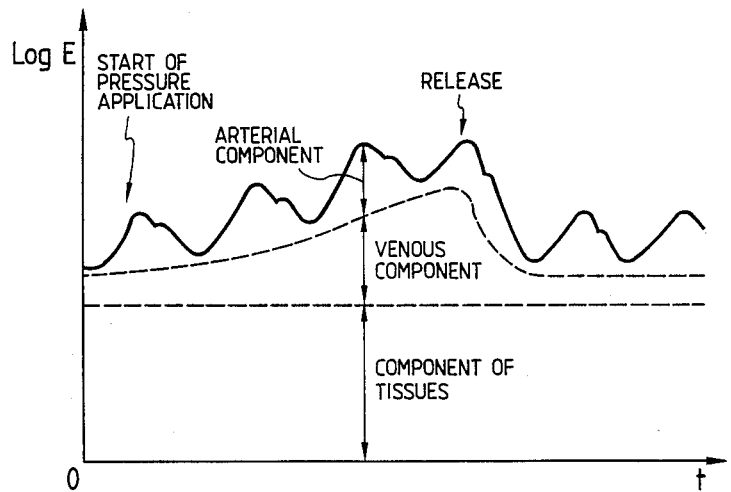
FIG. 4 is a graph showing a waveform of an output signal of a logarithmic amplifier with pressure application.

After the application of the pressure, the logarithm-converted venous signal Log E varies as shown in FIG. 4. The signal component of venous blood can be separated from those of arterial blood and tissues by utilizing the facts that frequency components of the waveform of venous blood is different from those of arterial blood and the signal component of tissues is time-invariant. Therefore, the venous blood constituent can be measured.

The venous blood constituent can be measured by another method which utilizes the variation of the venous signal component after releasing the pressure. After abrupt release of the pressure the venous signal component of vein varies faster than that during the application of pressure. The measurement of a blood constituent can be performed in the similar manner to the above method.

The following should be noted in connection with the present invention. Even if the artery $\underline{a}$ is influenced by the pressure application, so that its cross-section is a little changed, almost no change is caused in the flowing quantity of the arterial blood. Moreover, as the measuring part itself does not receive any pressure, the optical characteristics of the tissues in the measuring part is not changed, avoiding the measurement error due to the change of the optical characteristics thereof.

Embodiment 1

The first embodiment of the invention will be described hereinafter with reference to FIGS. 4 to 6. In this embodiment, the oxygen saturation of venous blood is measured by separating the venous signal component during the application of pressure. This embodiment has a constitution in which the oxygen saturation of arterial blood can also be measured.

Figure 5:
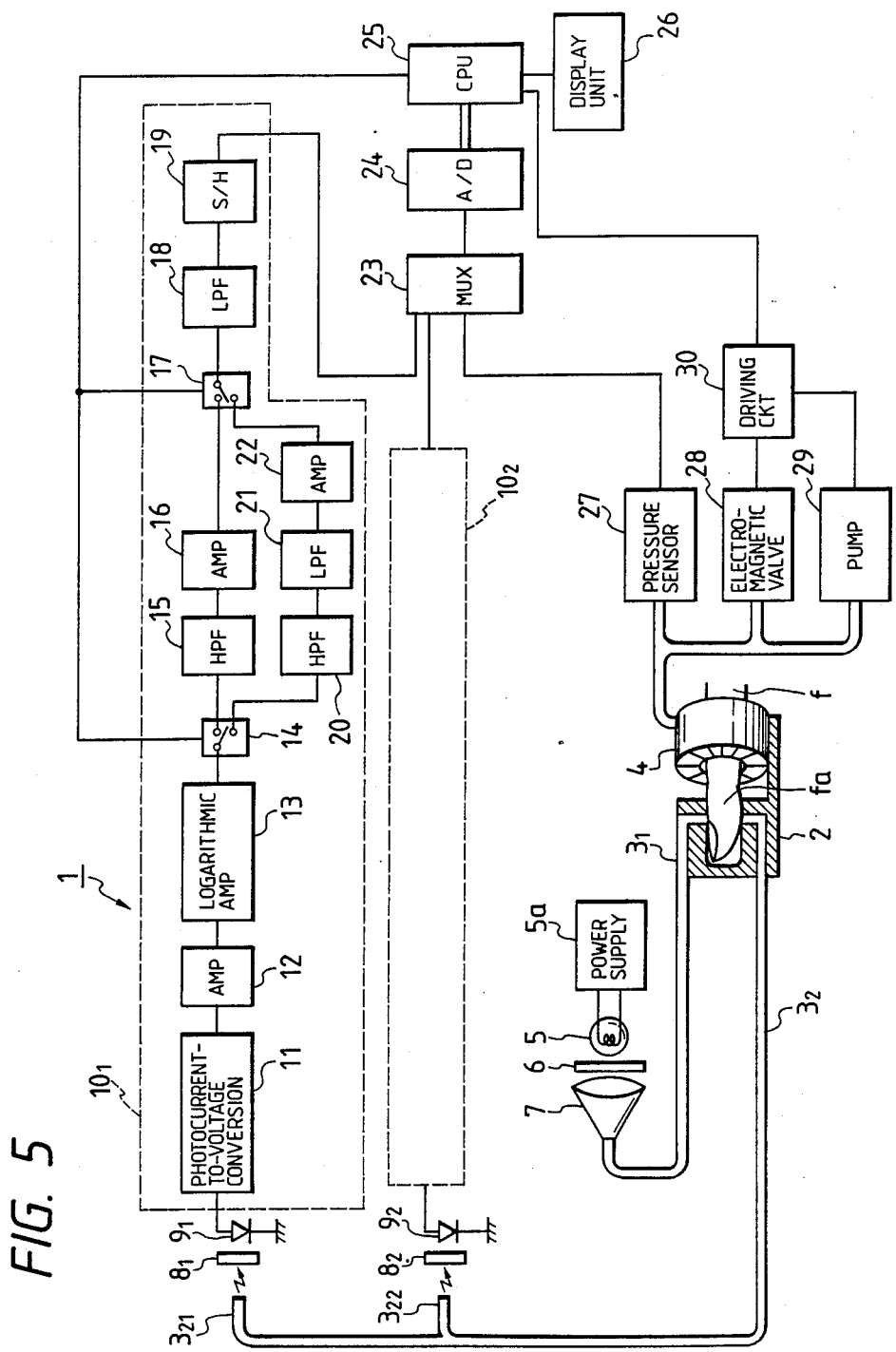
FIG. 5 is a block diagram showing an measuring apparatus of the oxygen saturation according to the first embodiment of the invention.
Figure 6:
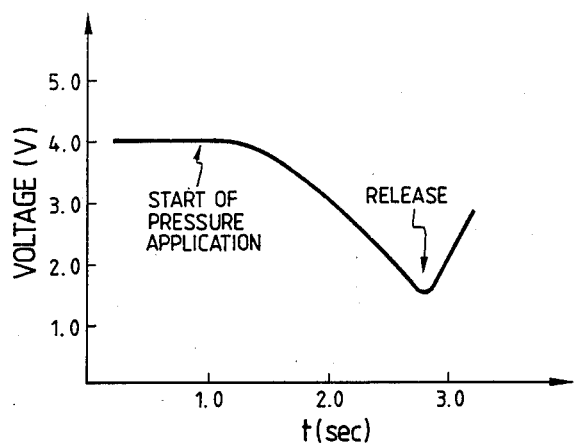
FIG. 6 is a graph showing a waveform of an output signal of an amplifier 22 with pressure application.

FIG. 5 is a block diagram showing the constitution of a measuring apparatus 1 according to this embodiment. A finger $\underline{f}$ of an object person is inserted into a probe 2 from the right side. Ends of optical fibers $3_1$ and $3_2$ are in contact with a top and a bottom portion of a tip (measuring part) $f_a$ of the inserted finger $\underline{f}$, respectively. The finger $\underline{f}$ is also inserted into a cuff 4 so that the pressure can be imposed on the finger $\underline{f}$ at the proximal portion from the measuring part by the cuff 4. A cuff of an "electronic sphygmomanometer for finger" is used as the cuff 4.

The optical fiber $3_1$ is for introducing a light beam emitted from a halogen lamp 5 (light source) to the measuring part $f_a$. The light beam emitted from the halogen lamp 5 is passed through a thermic-rays-cutting filter 6, focused by a focusing lens 7, and made incident on the incidence-end of the optical fiber $3_1$. The thermic-rays-cutting filter 6 is disposed to prevent the occurrence of a burn at the measuring part $f_a$. The reference numeral 5a denotes a power supply for the halogen lamp 5.

The other end of the optical fiber $3_2$ is separated into two ends $3_{21}$ and $3_{22}$. A light beam outputted from the optical fiber $3_{21}$ is transmitted through an interference filter $8_1$ with transmission wavelength $\lambda_1$ of 805 nm and detected by a photodiode (photodetector) $9_1$. On the other hand, a light beam outputted from the optical fiber $3_2$ is transmitted though an interference filter $8_2$ with transmission wavelength $\lambda_2$ of 650 nm and detected by a photodiode $9_2$.

The photodiodes $9_1$ and $9_2$ are connected to signal processing circuits $10_1$ and $10_2$, respectively. The signal processing circuit $10_1$ comprises: a photocurrent-to-voltage conversion circuit 11, an amplifier 12 for amplifying the converted voltage, and a logarithmic amplifier 13 for logarithm-converting an output of the amplifier 12. An output of the logarithmic amplifier 13 is changed-over by an analog switch 14 and provided to a high-pass filter (HPF) 15 or 20.

The HPF 15 has its cut-off frequency of 0.3 Hz and separates a ripple component (signal component of artery). The separated signal component is amplified by an amplifier 16. On the other hand, the HPF 20 (DC component elimination means) has its cut-off frequency of 0.003 Hz and separates the venous signal component. The signal component separated by the HPF 20 is then passed through a low-pass filter 21 (LPF: ripple component elimination means) to eliminate a ripple component and amplified by an amplifier 22.

Outputs of the amplifiers 16 and 22 are changed-over by an analog switch 17 and provided to an LPF 18. The LPF 18 has its cut-off frequency of about 16 Hz and eliminates hum components originating from a power supply. An output signal from the LPF 18 is provided to a sample hold (S/H) circuit 19. An output of the S/H circuit 19, that is, an output of the signal processing circuit 10₁ is provided to a multiplexer (MUX) 23. The constitution of the signal processing circuit 10₂ is the same as that of the signal processing circuit 10₁, and an output of the circuit 10₂ is also provided to the MUX 23.

The MUX 23 is connected to an analog-to-digital (A/D) converter 24. The A/D converter 24 is connected to a CPU 25. The CPU 25 has such functions as calculating the oxygen saturation of the arterial blood and the venous blood on the basis of the signals provided from the signal processing circuits 10₁ and 10₂, and changing-over the analog switches 14 and 17 in a linked motion. A display unit 26 is connected to the CPU 25 and displays the calculated results of the oxygen saturation.

Connected to the cuff 4 are a pressure sensor 27, an electromagnetic valve (pressure releasing means) 28, and a pump (pressure imposing means) 29. The pressure sensor 27 is for detecting air pressure in the cuff 4 (hereinafter called "cuff pressure"). The electromagnetic valve 28 is for exhausting the air to finish imposing the pressure. The pump 29 is for giving the pressure to the cuff 4. The electromagnetic valve 28 and the pump 29 are driven by a driving circuit 30 which is controlled by the CPU 25. The cuff pressure which has been detected by the pressure sensor 27 is sent to the CPU 25 through the MUX 23.

Next, the description will be made as to the measurement of the oxygen saturation of arterial blood.

In this case, the pressure is not imposed on the finger f by the cuff 4. The analog switches 14 and 17 are changed-over so that the output of the logarithmic amplifier 13 may be provided to the LPF 18 through the HPF 15 and amplifier 16.

The output of the photodiode 9₁ is converted to the voltage value by the photocurrent-to-voltage conversion circuit 11, the obtained voltage is amplified by the amplifier 12, and then logarithm-converted by the logarithmic amplifier 13. Only the ripple component is separated by the HPF 15 from the output signal of the logarithmic amplifier 13, and then amplified by the amplifier 16. The output signal of the amplifier 16 is subjected to the hum-component elimination in the LPF 18, and finally held by the S/H circuit 19. In the same manner, the output of the photodiode 9₂ is processed by the signal processing circuit 10₂ and held by the S/H circuit therein.

The signal components of arterial blood corresponding to the wavelengths $\lambda_1$ and $\lambda_2$, which are held in the respective signal processing circuits 10₁ and 10₂, are changed-over by the MUX 23, converted to the digital signals by the A/D converter 24, and then provided to the CPU 25. The CPU 25 calculates the ratio between the signals corresponding to $\lambda_1$ and $\lambda_2$ and determines the oxygen saturation $S_aO_2$ of arterial blood on the basis of the equation (5) described above. The calculated result is displayed on the display unit 26.

On the other hand, the measurement of the oxygen saturation of venous blood will be hereinafter described.

In this case, the analog switches 14 and 17 are changed-over so that the output of the logarithmic amplifier 13 may be provided to the LPF 18 through the HPF 20, LPF 21 and amplifier 22. Then, the CPU 25 closes the electromagnetic valve 28 and starts driving the pump 29 to increase the pressure in the cuff 4. The cuff pressure is sampled by the pressure sensor 27 while the pump 29 is operating. When the cuff pressure has reached 80 mmHg, the operation of the pump 29 is stopped. The pressure value of 80 mmHg coincides with the average minimum blood pressure of a normal person, at which value the venous blood stream is obstructed while the arterial one is not obstructed. Apparently, in the invention, the cuff pressure at which the pump operation is stopped is not restricted to 80 mmHg.

FIG. 4 shows a variation of the output of the logarithmic amplifier 13 in the signal processing circuit 10₁ in the case where the pressure is applied to the cuff 4. While the signal components of arterial blood and tissues have the same waveforms as those without the pressure application, the venous signal component varies with time.

From the output signal of the logarithmic amplifier 13 the DC component and the ripple component are eliminated by the HPF 20 and LPF 21, respectively, so that only the venous signal component is separated. The separated venous signal component is amplified by the amplifier 22, subjected to the hum-component elimination in the LPF 18, and held by the S/H circuit 19. FIG. 6 shows a variation of the output signal of the amplifier 22. In the same manner, in the signal processing circuit 10₂ the venous signal component corresponding to the wavelength $\lambda_2$ is separated and held in its S/H circuit.

The CPU 25 sequentially receives the venous signal components corresponding to $\lambda_1$ and $\lambda_2$, calculates the ratio between those signal components, and determines the oxygen saturation of venous blood $S_vO_2$ in the similar operation to that for the oxygen saturation of arterial blood. The calculated result of $S_vO_2$ is displayed on the display unit 26. When the signal voltage becomes less than the prescribed value (e.g., 1.5 V), the CPU 25 releases the electromagnetic valve 28 so that the pressure application to the cuff 4 may be finished.

The means for separating the venous signal component is not restricted to the combination of a HPF and an LPF. For example, the venous signal component may be separated by logarithm-converting the output signals of the photodetector before and during the pressure application and obtaining the difference of the two logarithm-converted signals.

Embodiment 2

Figure 8:
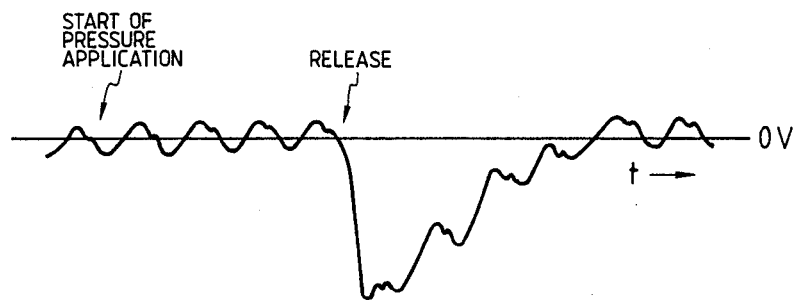
FIG. 8 shows a waveform of an output signal of a HPF 15 with pressure application.

The second embodiment of the invention will be described with reference to FIGS. 7 and 8.

In this embodiment, the oxygen saturation of venous blood is measured by extracting a venous signal component just after the abrupt releasing of pressure.

Figure 7:
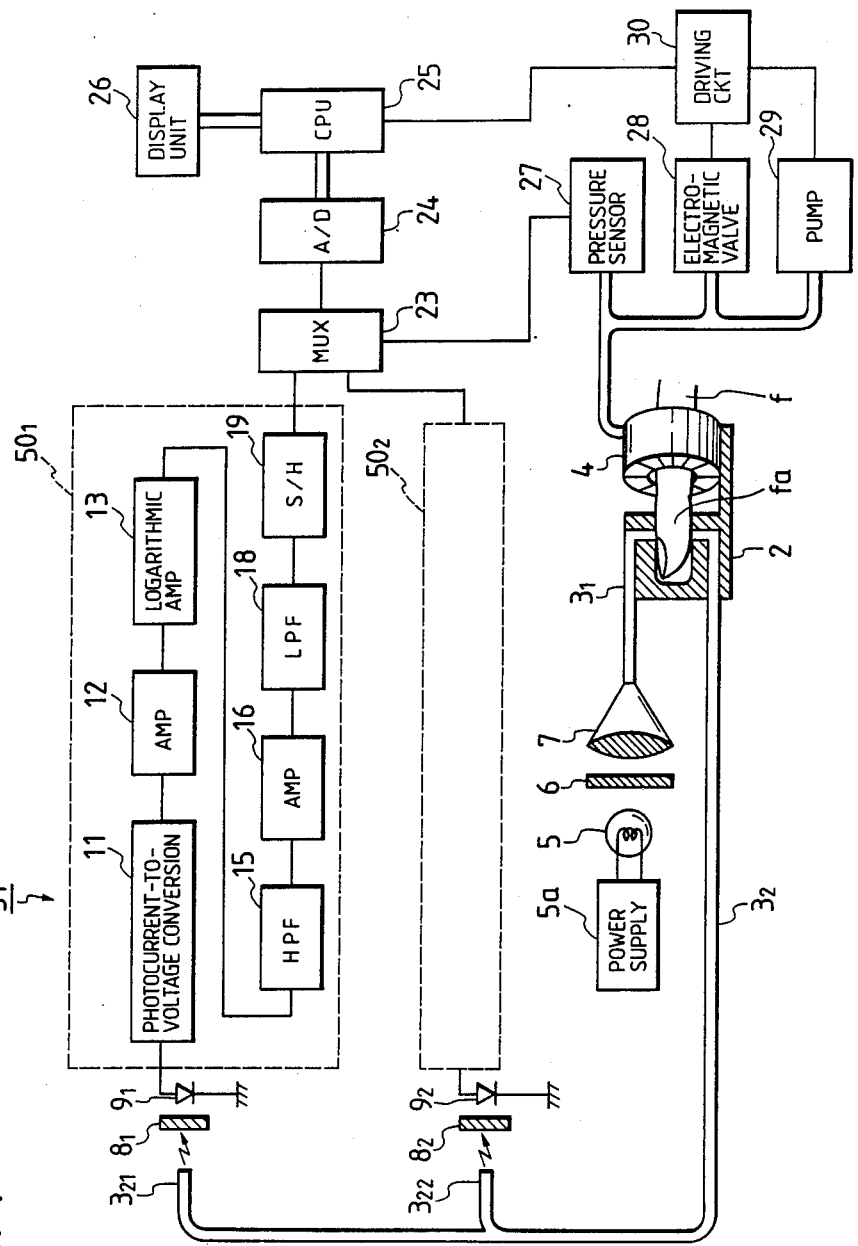
FIG. 7 is a block diagram showing an measuring apparatus of the oxygen saturation according to the second embodiment of the invention.

FIG. 7 is a block diagram showing the constitution of a measuring apparatus 51 according to the second embodiment of the invention. The same elements as those in FIG. 5 are designated by the respective same reference numerals and the redundant explanation will be omitted. The elements 11 to 19 are the same as those in FIG. 5 while the analog switches 14 and 17 in FIG. 5 are eliminated in FIG. 7. The HPF 15 has the same cut-off frequency as that in FIG. 5, that is, 0.3 Hz.

The measurement of the oxygen saturation of venous blood will be described.

The CPU 25 provides an instruction to the driving circuit so as to close the electromagnetic valve 28 and starts the pump 29 operating. The pressure of the cuff 4 is increased to a prescribed value, e.g., 80 mmHg, and the operation of the pump 29 is stopped. About one second after that, the electromagnetic valve 28 is opened and the pressure application to the finger f is released.

An this time of pressure release, the venous blood which has been stored in veins fast flows out, so that the transmission light quantity increases. Corresponding to the increase of the transmission light quantity, the output of the logarithmic amplifier 13 decreases as shown in FIG. 4. Since this decrease of the output, which is caused by the decrease of the venous signal component, is faster than the output variation during the pressure application, it passes through the HPF 15 with the cut-off frequency of 0.3 Hz. FIG. 8 shows a waveform of the output signal of the HPF 15. This output signal is amplified by the amplifier 16, subjected to the hum-component elimination in the LPF 18, and then held by the S/H circuit 19.

With the above-described procedure, the venous signal components corresponding to $\lambda_1$ and $\lambda_2$ are held by the respective signal processing circuits $50_1$ and $50_2$. The CPU 25 receives these signal components, calculates the oxygen saturation of venous blood $S_vO_2$ in the same manner as in the first embodiment, and displays the calculated result on the display unit 26.

Means for separating the venous signal component, in the invention, is not restricted to a HPF. The venous signal component may be separated by logarithm-converting the output signals of the photodetector before and after the pressure release and obtaining the difference between the logarithm-converted signals.

It is noted that since the variation of the venous signal component in the second embodiment is faster than that in the first embodiment, the second embodiment has an advantage that it hardly receives any influences (artifacts) caused by, e.g., a movement of the living body under measurement.

In the above first and second embodiment, one halogen lamp as the light source and two photodiodes as the photodetector are employed. However, the type and number of the light source and the photodector are not restricted to those in the two embodiments. For example, photodetected signals corresponding to plural wavelength components may be obtained by employing plural light sources with different wavelength components and one photodetector and changing-over the plural light sources successively. Or, plural light sources and plural photodetectors may be employed with one-to-one correspondence.

The optical fibers $3_1$ and/or $3_2$ may be eliminated by installing the light source and/or photodetectors near the measuring part and directly illuminating the measuring part and/or directly detecting the emergent light beams by the photodetectors.

In the above embodiments, the photodetected signal is logarithm-converted by the logarithmic amplifier 13 and then the venous signal signal component is separated by the HPF 20 and LPF 21, or the HPF 15. However, for example, the venous signal component may be separated by immediately converting the photodetected signal to a digital signal, providing it to a CPU, and performing operations of logarithm conversion and digital filtering in the CPU.

What is claimed is:

1. An apparatus for measuring a blood constituent in a living body, comprising:

light source means for illuminating a measuring part of said living body by at least two kinds of light beams with different wavelength components;

photodetecting means for detecting light beams transmitted from said measuring part;

logarithm-converting means for logarithm-converting photodetected signals outputted from said photodetecting means;

signal separation means for separating time-variant venous signal components corresponding to respective wavelength components from logarithm-converted signals;

pressure application means for applying pressure to a proximal portion from said measuring part; and computing means for controlling said pressure application means so that said pressure may change with a peak value being about the minimum blood pressure and calculating a venous blood constituent characteristic on the basis of said venous signal components separated by said signal processing means.

2. An apparatus as claimed in claim 1, wherein said pressure application means comprises:

a cuff for applying said pressure to said proximal portion from said measuring part;

pressure increasing means for increasing cuff pressure until about the minimum blood pressure; and pressure releasing means for fast decreasing said cuff pressure.

3. An apparatus as claimed in claim 2, wherein said signal separation means has a high-pass characteristic so as to pass said venous signal components corresponding to a period in which said cuff pressure is being fast decreased.

4. An apparatus as claimed in claim 1, wherein said venous blood constitution characteristic is the oxygen saturation.

5. An apparatus as claimed in claim 1, wherein said signal separation means comprises DC component elimination means and ripple component elimination means for eliminating arterial signal components.

6. A method for measuring a blood constituent in a living body, comprising the steps of:

applying pressure to a proximal portion from a measuring part of said living body so that said pressure may change with a peak value being about the minimum blood pressure;

illuminating said measuring part by at least two kinds of light beams with different wavelength components;

detecting light beams transmitted from said measuring part;

logarithm-converting photodetected signals;

separating time-variant venous signal components corresponding to respective wavelength components from logarithm-converted signals; and calculating a venous blood constituent characteristics on the basis of separated venous signal components.

7. A method as claimed in claim 6, wherein said venous blood constituent characteristic is the oxygen saturation.

8. A method as claimed in claim 6, wherein said step of applying pressure comprises the step of fast decreasing said pressure, and in said separating step said venous signal components corresponding to a period in which said pressure is being fast decreased are separated.

* * * * *